United States Patent [19]

Patel

[11] 4,214,582

[45] Jul. 29, 1980

[54] SURGICAL DRESSING

[75] Inventor: Harish A. Patel, Crystal Lake, Ill.

[73] Assignee: The Kendall Company, Boston, Mass.

[21] Appl. No.: 10,103

[22] Filed: Feb. 7, 1979

[51] Int. Cl.³ .............................................. A61L 15/00
[52] U.S. Cl. .................................................... 128/156
[58] Field of Search ............................... 128/155–156, 128/284, 287, 290 R, 290 W, 296; 428/170, 195, 284, 287, 288, 305

[56] References Cited

U.S. PATENT DOCUMENTS

| | | | |
|---|---|---|---|
| 3,067,747 | 12/1962 | Wolterding et al. | 128/296 |
| 3,542,634 | 11/1970 | Such et al. | 128/156 |
| 3,545,442 | 12/1970 | Wicker et al. | 128/156 |
| 3,949,130 | 4/1976 | Sabee et al. | 128/296 |
| 4,045,833 | 9/1977 | Mesek et al. | 128/287 |

*Primary Examiner*—C. Fred Rosenbaum
*Attorney, Agent, or Firm*—Powell L. Sprunger

[57] ABSTRACT

A surgical dressing comprising, a relatively nonadherent sheet comprising a nonwoven fabric having an outer surface defining a layer of substantially hydrophobic fibers. The dressing has a second relatively absorbent sheet comprising a multi-layered bulked open-mesh fabric. The first and second sheets are laminated together to form the dressing with the outer surface of the first sheet facing outwardly from the dressing.

7 Claims, 12 Drawing Figures

SURGICAL DRESSING

BACKGROUND OF THE INVENTION

The present invention relates to absorbent articles, and more particularly to surgical dressings.

A number of surgical dressings have been proposed in the past for use on patients. Although such dressings may be suitable for a particular application, the dressings have failed to account for the varying conditions of the patient's wound. The initial stage of wound healing is characterized by passage of relatively large amounts of body fluids, and it is thus necessary to provide a relatively absorbent dressing to capture the fluids during this stage of the healing process. Further, it is desirable that the dressing utilized during this stage be very porous, such that granulating tissue is permitted to grow into the dressing, and debris from the wound is removed with the dressing when withdrawn from the wound.

However, once the wound reaches the maturation stage and the effusion of body fluids diminishes, the dressing utilized during the initial state becomes inadequate for the wound and may disrupt the healing process. At this stage, the dressing should have absorbent characteristics, but should be relatively nonadherent to the wound.

SUMMARY OF THE INVENTION

A principal feature of the present invention is the provision of an improved surgical dressing of simplified construction.

The dressing of the present invention comprises, a first relatively nonadherent sheet comprising a nonwoven fabric having an inner layer of substantially hydrophilic fibers, a first surface layer of substantially hydrophobic fibers, and a second surface layer of substantially hydrophobic fibers on an opposed side of the inner layer relative to the first surface layer. The inner and surface layers are bonded together in substantially isolated highly compacted areas defining adjacent regions of substantially less compaction. The fabric is formed in a repeating series of wave-like undulations substantially throughout the dimensions of the fabric, with the interfiber spaces in the areas being substantially closed, and with the interfiber spaces in the regions being substantially open. The dressing has a second relatively absorbent sheet comprising an open-mesh, bulked, multi-layered woven fabric, with threads of the fabric being distorted into sinuous and tortuous configurations. The first and second sheets are laminated together to form the dressing with the first surface layer of the first sheet facing outwardly from the dressing.

A feature of the present invention is that the second sheet is relatively porous and has excellent absorbent characteristics.

Thus, a feature of the present invention is that the second sheet may be applied against a patient's wound during the initial stage of the healing process.

Still another feature of the invention is that the first sheet is absorbent and is relatively nonadherent to the patient's wound.

Thus, another feature of the invention is that the first sheet may be utilized to contact the patient's wound during a later stage of the healing process.

Another feature of the invention is that the dressing may be utilized during various stages of the healing process, and eliminates the necessity for inventories of multiple dressings.

A further feature of the invention is that the laminated dressing reduces the number of layers required for the fabric in the second sheet.

Yet another feature of the invention is that the first sheet provides a protective layer over the second sheet when the second sheet is applied against the patient's wound.

Yet another feature of the invention is that the first sheet reduces the number of loose threads which may be otherwise found in an edge of the second sheet when cut.

A further feature of the invention is that the second sheet reinforces the first sheet when the first sheet is utilized on the patient's wound in order to prevent tearing of the first sheet during use.

Further features will become more fully apparent in the following description of the embodiments of this invention and from the appended claims.

DESCRIPTION OF THE PREFERRED EMBODIMENTS

Figure 1:
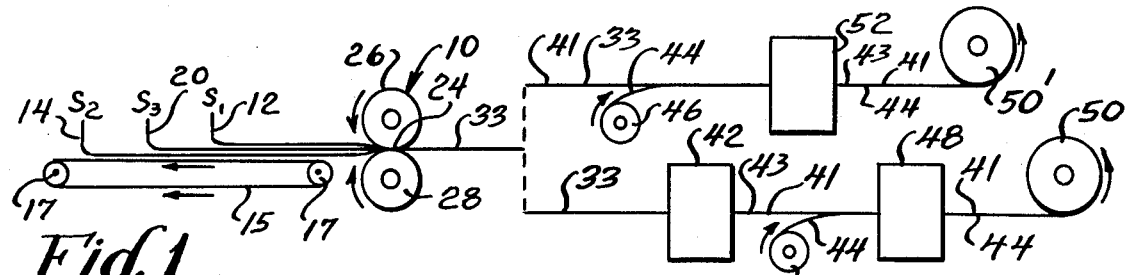
FIG. 1 is a diagrammatic view illustrating an apparatus for constructing a surgical dressing of the present invention.
Figure 1A:
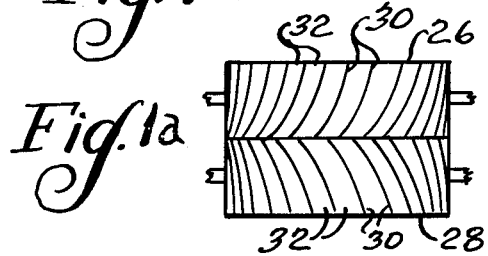
FIG. 1a is a diagrammatic view illustrating a pair of rolls in the apparatus of FIG. 1.

Referring now to FIGS. 1 and 1a, there is shown in diagrammatic form an apparatus generally designated 10 for constructing a nonwoven fabric and a surgical dressing of the present invention. The apparatus 10 may have suitable sources $S_1$ and $S_2$ which supply first and second outer or surface layers 12 and 14 of a heat-sensitive fibrous hydrophobic material to an endless belt 15 which is supported and driven by a pair of opposed rolls 17 in a direction as indicated by the arrows in the drawing. The layers 12 and 14 may be constructed from any suitable heat-sensitive hydrophobic fiber such as polypropylene or nylon, and, in a preferred form, the layers 12 and 14 comprise textile-length polyester fibers. Also, if desired, the surface of the fibers in layers 12 and 14 may be treated with a wetting agent to render them more hydrophilic, thus improving the fluid transfer rate and adsorbent capacity of the nonwoven fabric in the dressing without impairing the nonadherency of the dressing for a patient's wound. A suitable polyester fiber for use in the layers 12 and 14 having a solid hydrophilic finish is sold by Eastman Kodak Company, Rochester, New York, under the fiber product No. 432. The apparatus 10 also has a source $S_3$ of substantially hydrophilic fibers, such as a blend of hydrophobic fibers and predominant hydrophilic fibers, which is supplied to the belt 15 in the form of an inner or central layer 20 intermediate the outer layers 12 and 14. In a preferred form, the inner layer 20 comprises a blend or mixture of textile-length rayon fibers and textile-length polyester binder fibers, and the polyester fibers may be provided with a hydrophilic finish, as previously discussed in connection with the outer layers 12 and 14, if desired. In a suitable form, the inner layer 20 may comprise rayon fibers in a range of 20 to 99% by weight and polyester fibers in a corresponding range of 80 to 1% by weight, and a preferred range of 75 to 85% rayon fibers and 25% to 15% polyester fibers by weight. In a preferred form, the polyester binder fibers in the central layer 20 soften at a temperature lower than the fibers in the layers 12 and 14, and may comprise a 3.0 denier, 1½ inch polyester fiber, Type 450, sold by Celanese Fibers Marketing Company, New York, New York. Each of the outer layers 12 and 14 may have a weight approximating 20% of the total fabric weight, while the inner layer may have a weight approximating the remaining 60% of the fabric. Typically, for a fabric having a weight of 30 g./sq. yd. each of the outer layers 12 and 14 has a weight of 6 g./sq. yd. while the inner layer has a weight of 18 g./sq. yd.

As shown, the belt 15 passes the overlying layers 12, 20, and 14 to the nip 24 of a pair of opposed heated rolls 26 and 28 which are rotatably driven by suitable means in a direction as indicated by the arrows in the drawing. With reference to FIG. 1a, the layers are fused or bonded together in areas by heat and pressure as the layers pass between the rolls 26 and 28, which are both engraved with a pattern of helical lands 30 and grooves 32, in order to form a series or pattern of pressure areas of various extent in a nonwoven fabric 33. An apparatus disclosed in U.S. Pat. No. 3,507,943, incorporated herein by reference, may be utilized to accomplish this result.

Figure 3:
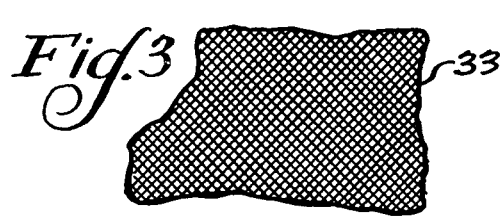
FIG. 3 is a fragmentary plan view illustrating a nonwoven fabric constructed by the apparatus of FIG. 1 in a stage prior to completion.
Figure 3A:
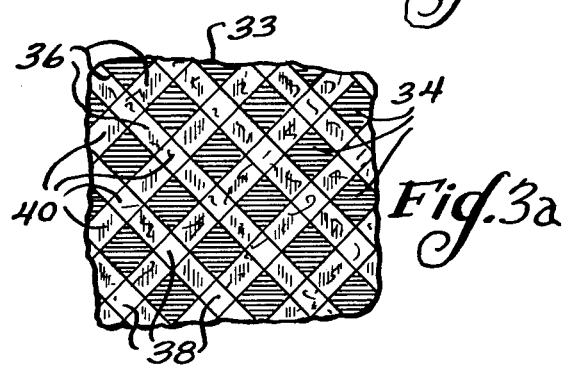
FIG. 3a is a fragmentary plan view of the fabric of FIG. 3 taken on an enlarged scale.

The characteristics of the fiber displacement pattern in the fabric 33 resulting from fusion of the fibers by the rolls 26 and 28 will be discussed in connection with FIGS. 3 and 3a. As shown, the bonded fabric 33 has highly compacted and fused areas 34 at locations where a land on the roll 26 has traversed a land on the roll 28. The nonwoven fabric 33 also has intermediately compressed areas 36 where a land on one roll has traversed a groove on the other roll. The fabric 33 also has substantially noncompacted areas 38 where a groove on one roll has traversed a groove on the other roll. The areas 34, 36, and 38 are in the form of quadrilaterals with parallel sides, although adjacent sides may not have equal lengths, and hence the areas may be termed rhomboidal. As shown, the combined areas 36 and 38 define relatively noncompacted and unbonded regions 40 which surround and isolate each of the bonded areas 34, with the spaced areas 34 having interfiber spaces substantially closed during fusion by the rolls. While the fabric shown in the drawings has an inner layer located between a pair of outer hydrophobic layers, it will be understood that a single outer layer of hydrophobic fibers may be utilized to define an outer surface of the fabric, if desired.

With reference to the lower right-hand portion of FIG. 1, the bonded nonwoven fabric 33 is then passed to a compacting device 42 which microcrepes and bulks the fabric 33 into a micrexed nonwoven fabric 43. The device 42 may be of any suitable type, such as an apparatus disclosed in U.S. Pat. No. 3,260,778, incorporated herein by reference. In a alternative form, the device 42 may be any suitable apparatus which softens the fabric 33.

Figure 7:
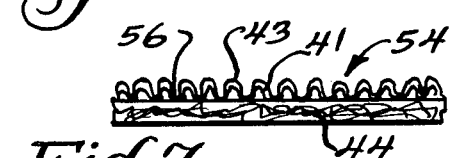
FIG. 7 is a fragmentary sectional view of another embodiment of the surgical dressing of the present invention.
Figure 7A:
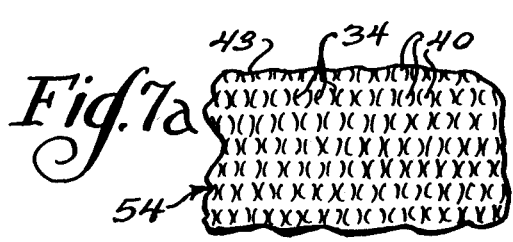
FIG. 7a is a fragmentary plan view of a nonwoven fabric utilized in the surgical dressing of FIG. 7.

With reference to FIG. 7a, the micrexing or compacting procedure causes the interfiber spaces in the unbonded regions 40 of the fabric 43 to become substantially open without destroying the structural integrity of the fused areas 34. Thus, the regions 40 have relatively open interfiber spaces for enhanced absorbency in the fabric 43, since the absorbency is largely dependent upon the spacing between the fibers. In this regard, the fabric 33 typically has an absorbent capacity approximating six times its own weight, while the absorbent capacity of the fabric 43 typically has an increased absorbent capacity approximately eleven times its own weight after the micrexing operation. In addition, the interfiber spaces in the fused areas 34 remain substantially closed, and the closed areas 34 in combination with the outer layers of hydrophobic fibers provides a nonadherent surface for contacting a patient's wound. In addition, the micrexing operation results in formation of the fabric into a repeating series of wave-like undulations substantially throughout the length of the fabric, with the undulations extending across the width of the fabric. Thus, the fabric assumes a very bulky configuration in order to provide a soft and conformable sheet in the dressing with cushioning characteristics for added comfort to the patient.

The following example is illustrative of a nonwoven fabric which may be utilized as a surgical dressing according to the present invention:

EXAMPLE:

An array of fiber layers comprising a pair of outer or surface layers of 100% 1.5 denier, 1½" polyester fibers, each being approximately 20% of the total fabric weight (gms/sq. yd.), are placed around an inner core layer comprising 85% 1.5 denier 1 9/16" rayon fibers and 15% 3.0 denier, 1½" polyester binder fibers, with the inner layer being approximately 60% of the total fabric weight, and the layers bonded with heat and pressure as previously described in connection with FIGS. 1 and 1a. The layered fabric is then treated with a mechanical compactor, such as disclosed in U.S. Pat. No. 3,260,778, in order to impart a repeating series of wave-like undulations substantially throughout the fabric length and width and to open the interfiber spaces of the nonbonded regions. The resulting fabric weighs approximately 37.6 gms/sq. yd., and has a thickness of 26.0 mils (as measured by the Ames-Mercer gauge), a bulk of 14.7 cm.$^3$/gm., and an absorbent capacity of approximately 1100%. The comparative figures of the fabric prior to micrexing are as follows: 34 gm/sq. yd., a thickness of 12.5 mils, a bulk of 7.85, and an absorbent capacity of 640%.

With reference again to the lower right-hand portion of FIG. 1, a second sheet or web 44 of an absorbent material is unwound from a roll 46, and is placed against a surface of a first sheet 41 comprising the micrexed nonwoven fabric 43. As shown, the first and second sheets 41 and 44 are supplied to a suitable device 48 which laminates the sheets 41 and 44 together. In a suitable form, the device 48 may supply heat in order to melt the heat-sensitive fibers adjacent the second sheet 44, and fuse the sheets 41 and 44 together. In an alternative form, the device 48 may supply adhesive as the second sheet 44 is placed against the first sheet 41 in order to bond the sheets together. As shown, the laminated sheets 41 and 44 pass from the device 48, and are wound into a suitable roll 50 for subsequent handling.

Figure 4:
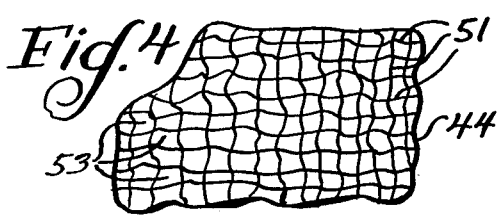
FIG. 4 is a fragmentary plan view of an open-mesh fabric which is utilized in the dressing of the present invention.

The second sheet 44 comprises a gauze fabric or an openmesh, bulked multi-layered, woven fabric with threads 51 of the fabric being distorted into sinuous and tortuous configurations, as shown in FIG. 4, defining relatively large open spaces 53 between the threads 51, and the sheet 44 may comprise a washed gauze sponge, as disclosed in U.S. Pat. Nos. 2,081,370 and 3,190,289, incorporated herein by reference. As disclosed therein, the fabric may be constructed from especially treated tobacco or cheese cloth, rayon or mixtures of the two to give it a pronounced three-dimensional structure as contrasted to the substantially planar structure of ordinary gauze. The preferred open-mesh cloth for the dressing of this invention may be made of 20s to 60s yarn size with range of 30s to 40s being preferred. The twist multiple (turns per inch over square root of yarn number) of the yarn may range from 3 to 7 with the warp yarns preferably having a slightly higher twist multiple than the filler yarns. It is preferred that the warp yarns have a twist multiple in the range of 4.25 to 5.0 with the filler yarns having a twist multiple of about 4. The thread count may vary from about $8 \times 8$ mesh to about $18 \times 12$ mesh with the optimum about $14 \times 8$ mesh before treatment. The material may be subjected to standard bleaching procedures and the cotton may additionally be subjected to standard boiling procedures.

The bleached tobacco cloth or cheese cloth as above described may be immersed in a water bath, preferably a hot bath in the presence of detergent, and while it is immersed or saturated it is strongly agitated causing at least the warp threads to assume sinuous or tortuous formations while the fabric shrinks and becomes thick and bulky. The bulkiness, and the configurations which the warp and weft threads assume, is set in the drying process. These configurations of the threads of the fabric are retained in the dried fabric and persist to a substantial extent even when the fabric is wetted again with exudate from a wound. It is possible to obtain a fabric in which the number of e bends is very great and such a fabric is satisfactory for the dressings of this invention, although it is preferred to stop the processing just short of the formation of e bends. Preferably, the fabric threads of the second sheet comprise a hydrophilic material, such as cotton, rayon, or a cotton-rayon blend. Alternatively, the threads of the second sheet may comprise a thermoplastic material, such as polypropylene fibers or polyester fibers treated with a hydrophilic finish.

In alternative form, as illustrated in the upper right-hand portion of FIG. 1, the second sheet 44 may be unwound from the roll 46 and placed against the first sheet 41 comprising the nonwoven fabric 33. The first and second sheets 41 and 44 are passed to a device 52 which laminates the sheets 41 and 44 together, such as by the application of adhesive as the second sheet 44 is placed against the first sheet 41, and microcrepes or micrexes the first sheet 41 after placement of the second sheet 44 against the first sheet 41. The compacting device 42 previously discussed may be utilized in the device 52 to perform the micrexing operation in the device 52. As shown, the laminated and microcreped sheets 41 and 44 are wound into a suitable roll 50'.

Figure 2:
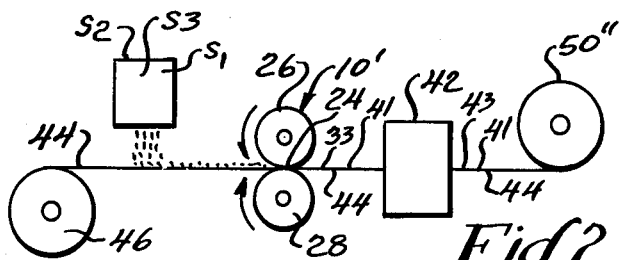
FIG. 2 is a diagrammatic view illustrating another apparatus for constructing a surgical dressing of the present invention.

An alternative apparatus 10' for constructing the surgical dressing is illustrated in FIG. 2, in which like reference numerals designate like parts. In this device, the second sheet 44 of absorbent fabric is unwound from the roll 46, and the sources $S_1$, $S_2$, and $S_3$ of fibers place the fibrous layers on the second sheet 44 after which the second sheet and overlying fibrous layers are passed to the nip 24 of the rolls 26 and 28, as previously discussed in connection with FIGS. 1 and 1a. Thus, the rolls 26 and 28 form bonded and unbonded regions in the fibrous layers, as previously discussed in connection with FIGS. 3 and 3a, while simultaneously fusing the fibrous layers to the second sheet through the medium of the fused heat-sensitive fibers in the fused areas 34. The laminated first nonwoven sheet 41 and second absorbent sheet 44 are then passed to a device 42 which microcrepes the nonwoven fabric 33 in a manner as previously described in connection with FIG. 1, after which the first and second sheets 41 and 44 are wound into a suitable roll 50''. Thus, the surgical dressing may be constructed in alternative manners as discussed in connection with FIGS. 1 and 2, and, for convenience, the resulting rolls 50, 50' and 50'' will be designated by the common reference numeral 50.

With reference to FIGS. 7 and 7a, the rolls 50 may be cut to suitable length in order to form surgical dressings generally designated 54 of the present invention. As shown, the dressing 54 has the first sheet 41 comprising the micrexed nonwoven material 43 formed into a repeating series of wave-like undulations substantially throughout the dimensions of the fabric. The dressing 54 also has the second sheet 44 of open-mesh woven fabric, with the first and second sheets 41 and 44 being laminated together by suitable means 56 at their joining surface, such as adhesive or fusion of the fibers in the first sheet 41, as previously discussed. In suitable form, the second sheet 44 may comprise one to three plies of the open-mesh woven fabric, with the first sheet decreasing the number of plies in the second sheet normally required for a surgical sponge.

In use, the second sheet 44 of the dressing 54 is placed against a patient's wound during the initial stage of the healing process. The second sheet 44 is highly absorbent and permits the body fluids to readily pass into the dressing 54. At the same time, the first sheet 41 provides a protective layer for the second sheet 44 when placed against the wound. Further, the first sheet 41 provides an aesthetically pleasing appearance for the dressing 54 when utilized in this manner, and also minimizes loose threads which may otherwise appear in cut edges of the second sheet 44. During the initial stage of the healing process, the porous second sheet 44 permits desired ingrowth of granulating tissue in order to permit removal of debris from the wound when the dressing is removed from the patient. Further, the second sheet 44 provides a relatively high rate of fluid transfer into the dressing, and the second sheet 44 is relatively bulky and conformable in order to provide softness for the dressing and apply pressure to the wound during use.

During a later stage in the healing process when the rate of fluid passage from the wound has diminished, the first sheet 41 of the dressing 54 may be placed against the patient's wound. The first sheet 41 provides sufficient absorbency for this stage of the healing process, and the first sheet 41 is relatively nonadherent to the wound and minimizes the growth of tissue into the dressing which is desired at this stage of the healing process. During use of the dressing in this manner, the second sheet 44 reinforces the first sheet 41, and prevents tearing of the relatively weak first sheet 41.

Thus, in accordance with the present invention, the first and second sheets 41 and 44 cooperate with each other to define an improved surgical dressing for use in various stages of a healing process. Further, the dressing 54 of the present invention eliminates the necessity for maintaining inventories of separate dressings which must otherwise be selected for use during different stages of the healing process.

Figure 8:
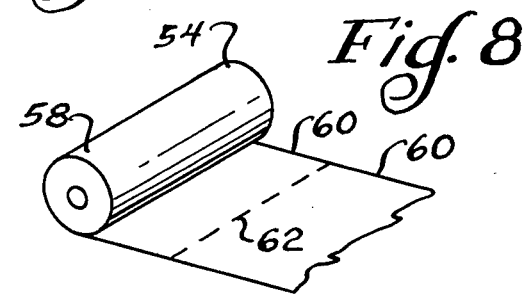
FIG. 8 is a fragmentary perspective view of a surgical dressing being illustrated in the form of a roll.
Figure 9:
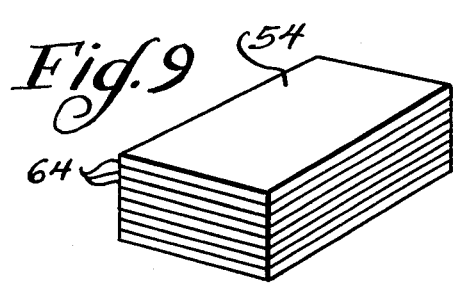
FIG. 9 is a perspective view of the surgical dressing being illustrated in the form of multiple sheets.

With reference to FIG. 8, the dressing 54 may be supplied to the physician in the form of a roll 58 in which separate sheets 60 of the dressing 54 may be severed along suitable perforation lines 62 extending at spaced intervals across the length of the dressing. In an alternative form, as shown in FIG. 9, the dressings 54 may be supplied in the form of stacked sheets 64 of suitable size.

Figure 5:
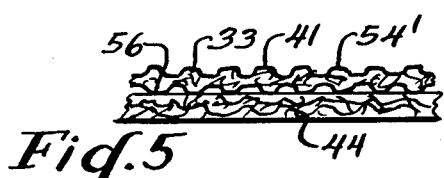
FIG. 5 is a fragmentary sectional view illustrating a surgical dressing of the present invention.
Figure 6:
FIG. 6 is a fragmentary sectional view of another embodiment of the surgical dressing of the present invention.

Although in a preferred form the dressing 54 utilizes the microcreped nonwoven fabric 43 previously discussed in connection with FIGS. 1–3a, 7, and 7a, the surgical dressing may utilize the nonmicrexed nonwoven fabric 33. Thus, with reference to FIG. 5, in which like reference numerals designate like parts, the dressing 54' has a first sheet 41 comprising the nonwoven fabric 33 prior to micrexing, with the sheet 41 being laminated to the second sheet 44 in a suitable manner, such as by the application of adhesive or heating, as previously discussed. In an alternative form, as shown in FIG. 6, in which like reference numerals designate like parts, the dressing 54" has the first sheet 41 comprising a plurality of layers of the nonwoven fabric 33 prior to micrexing, with the layers of the first sheet 41 and second sheet 44 being laminated together, as previously described. Of course, it will be understood that multiple layers of the micrexed nonwoven fabric 43 may be utilized to form the first sheet 41 which is laminated to the second sheet 44 in a manner as previously discussed in connection with FIGS. 7 and 7a.

The foregoing detailed description is given for clearness of understanding only, and no unnecessary limitations should be understood therefrom, as modifications will be obvious to those skilled in the art.

I claim:

1. A surgical dressing, comprising:
   a first relatively nonadherent sheet comprising a nonwoven fabric having an inner layer of substantially hydrophilic fibers, and a surface layer of substantially hydrophobic fibers, said inner and surface layers being bonded together in substantially isolated highly compacted areas defining adjacent regions of substantially less compaction; and
   a second relatively absorbent sheet comprising an open-mesh, bulked, multi-layered, woven fabric with threads of the fabric being distorted into sinuous and tortuous configurations, said first and second sheets being laminated together to form the dressing with the surface layer of the first sheet facing outwardly from the dressing.

2. The dressing of claim 1 wherein the fabric of the first sheet is formed into a series of wave-like undulations, with the interfiber spaces in the areas being substantially closed, and with the interfiber spaces in the regions being substantially open.

3. The dressing of claim 1 wherein the fabric of the first sheet includes a second surface layer of substantially hydrophobic fibers on an opposed side of said inner layer relative to said first surface layer, said second surface layer being bonded in said areas and having open interfiber spaces in said regions.

4. The dressing of claim 3 wherein said first and second sheets are fused together.

5. The dressing of claim 1 wherein the hydrophobic fibers have a hydrophilic finish on surfaces thereof.

6. A surgical dressing, comprising:
   a first relatively nonadherent sheet comprising a nonwoven fabric having an inner layer of substantially hydrophilic fibers, a first surface layer of substantially hydrophobic fibers, and a second surface layer of substantially hydrophobic fibers on an opposed side of said inner layer relative to said first surface layer, said inner and surface layers being bonded together in substantially isolated highly compacted areas defining adjacent regions of substantially less compaction, said fabric being formed in a repeating series of wave-like undulations substantially throughout the dimensions of the fabric, with the interfiber spaces in said areas being substantially closed, and with the interfiber spaces in said regions being substantially open; and
   a second relatively absorbent sheet comprising an open-mesh, bulked, multi-layered, woven fabric with threads of the fabric being distorted into sinuous and tortuous configurations, said first and second sheets being laminated together to form the dressing with the first surface layer of the first sheet facing outwardly from the dressing.

7. A surgical dressing, comprising:
   a first relatively nonadherent sheet comprising a nonwoven fabric having an inner layer of substantially hydrophilic textile-length fibers comprising a blend of rayon and polyester fibers, and first and second surface layers of heatsensitive substantially hydrophobic textile-length polyester fibers on opposed sides of said inner layer, said inner and surface layers being fused together in relatively small bonding areas defining adjacent unbonded regions of the fibers isolating said areas from each other, said fabric being formed in a repeating series of wave-like undulations substantially throughout the fabric with the interfiber spaces in said regions being substantially open and with the interfiber spaces in said areas being substantially closed; and
   a second relatively absorbent sheet comprising an open-mesh, bulked, multi-layered, woven fabric with threads of the fabric being substantially cotton and distorted into sinuous and tortuous configurations, said first and second sheets being laminated together to form the dressing with the first surface layer of the first sheet facing outwardly from the dressing.

* * * * *